United States Patent [19]
Guerret et al.

[11] Patent Number: 4,463,004
[45] Date of Patent: Jul. 31, 1984

[54] DIOXAZABICYCLIC DERIVATIVES

[75] Inventors: Patrick G. Guerret, Rueil Malmaison; Bernard P. Bucher, Marnes la Coquette; Philippe L. Dostert; Gisèle C. Mocquet, both of Paris; Alain L. Nedelec, Colombes, all of France

[73] Assignee: Delalande S.A., Courbevoie, France

[21] Appl. No.: 368,924

[22] Filed: Apr. 16, 1982

[30] Foreign Application Priority Data

Apr. 21, 1981 [FR] France ................. 81 07904
Mar. 31, 1982 [FR] France ................. 82 05553

[51] Int. Cl.³ .................. A61K 31/535; C07D 491/08
[52] U.S. Cl. ........................ 424/248.5; 260/330.8;
424/248.51; 424/248.53; 424/248.54;
424/248.55; 424/248.56; 424/248.57; 544/105
[58] Field of Search ............ 544/105; 260/330.8;
424/248.5, 248.51, 248.53, 248.54, 248.55,
248.56, 248.57, 248.58

[56] References Cited

PUBLICATIONS

The Ring Index, Second Edition, Chemical Abstracts Service, (1960), p. 161.
May et al., Chemical Abstracts, vol. 68, (1968), 85834b.
May et al., "Cholinergic Receptor I. Cholinomimetic Activities of Some Analogs of cis-2-Methyl-4-dimethylaminomethyl-1,3-dioxolane Methiodide", *Journal of Pharmaceutical Sciences*, vol. 57, No. 3, Mar. 1968, pp. 511-513.
Vogel et al., "Protective Effects of Dimethyl-Propranolol (UM-272) During Global Ischemia of Isolated Feline Hearts", *J. Pharm. Exp. Therap.*, vol. 212, 1980, pp. 560-568.
Gibson et al., "Electrophysiologic Effects of UM-272 on Myocardial Ischemia in the Canine Heart", *J. Pharm. Exp. Therap.*, vol. 207, 1978, pp. 304-310.

*Primary Examiner*—Richard Raymond
*Attorney, Agent, or Firm*—Flynn, Thiel, Boutell & Tanis

[57] ABSTRACT

Compounds having analgesic activity are disclosed which have the general formula:

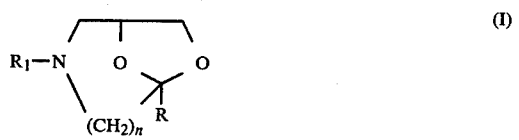

wherein $R_1$ is hydrogen, alkyl having 1 to 4 carbon atoms, cyclohexyl or benzyl; R is selected from the group consisting of alkyl having at least 4 carbon atoms; cyclohexyl; unsubstituted phenyl or phenyl substituted with one or more halogen atoms, methyl, methoxy, hydroxy, cyano, nitro, trifluoromethyl, carboxyl, ethoxycarbonyl, acetamido, methylsulfonyl, phenoxy, benzoyl, phenyl, α-hydroxybenzyl, cyclohexyl or carbamoyl; thienyl; pyridyl; naphthyl; naphthyl substituted with methoxy; adamantyl; and benzyl; and n is 1, 2 or 3, with the provisos that (1) when R is carboxyphenyl, benzoylphenyl, or (α-hydroxybenzyl) phenyl, n is not 3, and (2) when R is (α-hydroxy benzyl) phenyl, $R_1$ is not benzyl, and acid addition salts thereof.

21 Claims, No Drawings

DIOXAZABICYCLIC DERIVATIVES

The present invention relates to new dioxazabicyclic derivatives, a process for preparation thereof and the application of same in therapeutics.

These new derivatives correspond more precisely to the general formula:

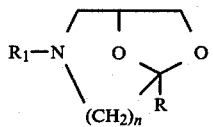
(I)

in which:
R₁ represents a hydrogen atom, an alkyl group with 1 to 4 carbon atoms, a cyclohexyl group or a benzyl group;
R represents an alkyl group comprising at least 4 carbon atoms; a cyclohexyl group; a phenyl nucleus substituted or not by one or more halogen atoms or by a methyl, methoxy, hydroxy, cyano, nitro, trifluoromethyl, carboxyl, ethoxycarbonyl, acetamido, methylsulfonyl, phenoxy, benzoyl, phenyl, α-hydroxy-benzyl, cyclohexyl or carbamoyl group; a thienyl, pyridyl or naphthyl nucleus, the latter being substituted or not by a methoxy group; or an adamantyl or benzyl group; and
n takes the value 1, 2 or 3, n only being able however to take on the value 1 or 2 when R represents a carboxyphenyl, benzoylphenyl or (α-hydroxybenzyl) phenyl group;
R₁ however not being able to represent a benzyl nucleus when R designates a (α-hydroxy benzyl) phenyl nucleus.

The present invention also relates to the mineral or organic acid addition salts of the derivatives of formula (I) and more especially those which are compatible with use in therapeutics. As mineral acid, hydrochloric acid may be cited as an example and as organic acid, maleic acid may be mentioned for example.

Among the derivatives of formula (I) there may be more especially mentioned those for which $R_1=H$ and $n=1$ or 3 as well as those for which $R_1=$benzyl and $n=3$, and among these latter more particularly the compounds for which R represents a thienyl, β-naphthyl, (methoxy-6) β-naphthyl or paraacetamidophenyl nucleus or a phenyl nucleus substituted or not by one or more halogen atoms or by a methyl, methoxy, hydroxy, cyano, nitro or trifluoromethyl group.

The present invention further relates to the processes for preparing the formula (I) derivatives.

A/ The process for preparing the formula (I) derivatives for which n takes the value 1 or 2, except those where R=carboxyphenyl or (α-hydroxybenzyl) phenyl, consists of:
either treating the compounds of formula:

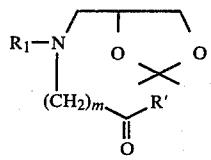
(II)

in which R' and R₁ have the same meanings respectively as R and R₁ in formula (I), R' not however being able to represent the carboxyphenyl or the (α-hydroxybenzyl) phenyl group, and m takes the value 1 or 2, preferably at reflux in benzene and in the presence of water, with hydrated paratoluenesulfonic acid,
or treating the compounds of formula (IIa) or (IIb), these compounds being in equilibrium according to the diagram:

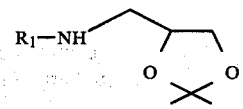

(IIa)          (IIb)

in which m, R₁ and R' have the same meanings as in formula (II), preferably at reflux in benzene or toluene, with paratoluenesulfonic acid, while progressively removing the water formed.

The compounds of formula (IIa) or (IIb) are obtained by the action of dilute hydrochloric acid (preferably 2N), in the presence of acetone, on the compounds of formula (II).

These latter are obtained by condensing, in an autoclave, preferably at 80°–100° C., or in an ethanol solution at room temperature and in the presence of triethylamine, or else at reflux in an aprotic solvent such as benzene, toluene, acetone, DMF or acetonitrile, in the presence of potassium carbonate, the compounds of formula:

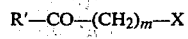
(III)

where R₁ has the same meaning as in formula (I), which compounds (III) are prepared according to the conventional methods described in the literature, with the compounds of formula:

$$R'—CO—(CH_2)_m—X \quad (IV)$$

in which R' and m have the same meanings as in formula (II), X representing a halogen atom or a tosyloxy or mesyloxy group.

B/ The process of the invention for preparing the derivatives of formula (I), for which n takes the value 3 and R₁ represents an alkyl group comprising 1 to 4 carbon atoms, cyclohexyl or benzyl group, consists of heating, preferably to about 160° C. in the presence of tri-n-butylamine, the compounds of formula:

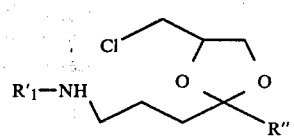
(V)

in which R″ has the same meanings as R in formula (I), but cannot however represent a carboxyphenyl, (α-hydroxybenzyl) phenyl or benzoylphenyl group, and R′₁ represents an alkyl group comprising 1 to 4 carbon atoms or a cyclohexyl or benzyl group.

The compounds of formula (V) are obtained by condensing the compounds of formula:

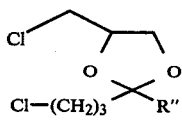     (VI)

in which R″ has the same meanings as in formula (V) with the amines of formula:

R′₁NH₂     (VII)

where R′₁ has the same meanings as in formula (V), the compounds of formula (VI) being obtained by condensing the compounds of formula:

R″—CO—(CH₂)₃—Cl     (VIII)

in which R″ has the same meanings as in formula (VI) with 3-chloro-1,2-propanediol, preferably in a methylene chloride medium, in the presence of

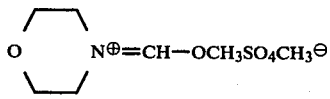

C/ The derivatives of formula (I) for which n=3 and R₁ represents the hydrogen atom may be obtained by debenzylation of the derivatives of formula (I) for which R₁ represents the benzyl group and n=3. This debenzylation may be more particularly obtained by catalytic hydrogenolysis, the catalyst being palladium on charcoal, or by action of the sodium-liquid ammonia mixture.

D/ The derivatives of formula (I) for which n=1 or 2 and R₁=H, except those for which R=(α-hydroxybenzyl) phenyl or benzoylphenyl, may also be obtained as in process C/ above, but from the corresponding derivatives of formula (I) for which R₁=benzyl.

Similarly, the derivatives of formula (I) for which R represents the (α-hydroxybenzyl) phenyl group, n=1 or 2 and R₁=H are obtained as in process C/ but from the corresponding derivatives of formula (I) for which R₁=benzyl and R=benzoylphenyl.

E/ The compounds of formula (I) for which R₁ represents an alkyl group comprising 1 to 4 carbon atoms or the cyclohexyl group, except those for which R=carboxyphenyl, carbamoylphenyl or acetamidophenyl may also be obtained by the so-called "PHASE TRANSFER" reaction in the presence of a so-called "PHASE TRANSFER" catalyst (such as tetra n-butyl-ammonium hydrogenosulfate or benzyl tri-n-butylammonium bromide) between the corresponding derivatives of formula (I), for which R₁ represents the hydrogen atom, and methyl or ethyl sulfate or the derivatives of formula:

R″₁—X     (IX)

in which R″ represents an alkyl group comprising 1 to 4 carbon atoms or the cyclohexyl group and X represent a halogen atom or a tosyloxy or mesyloxy group.

F/ The formula (I) derivatives for which R represents the pyridyl group and n takes the value 1 or 2, except those where R₁ represents the hydrogen atom, are obtained by cyclizing in the presence of triethylamine, preferably by heating in toluene, the compounds of formula:

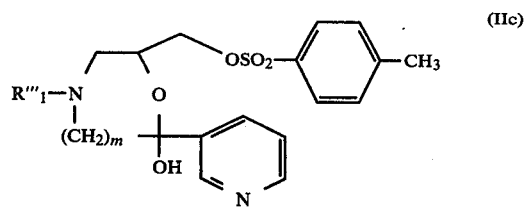     (IIc)

in which R‴₁ has the same meaning as R₁ in formula (I), without however being able to represent the hydrogen atom, and m=1 or 2, the compounds (IIc) being obtained by the action of tosyl chloride in a pyridine medium on the corresponding formula (IIb) or (IIa) compounds.

G/ The formula (I) derivatives for which R represents the carboxyphenyl group are obtained by saponifying, preferably with sodium ethylate in ethanol, the corresponding formula (I) derivatives for which R represents the (ethoxycarbonyl) phenyl group.

H/ The formula (I) derivatives for which R₁ represents the hydrogen atom and R represents the benzoylphenyl group are obtained by oxidizing, preferably with manganese dioxide and in a chloroform medium, the corresponding formula (I) derivatives for which R represents the (α-hydroxybenzyl) phenyl group.

The formula (I) derivatives may be salified according to the usual methods. Salification may for example be obtained by the action on these formula (I) derivatives, dissolved in an organic solvent such as acetone or ethanol, of an acid, such as hydrochloric acid or maleic acid, in solution in an organic solvent such as acetone or ethanol.

The following preparations are given by way of example to illustrate the invention.

EXAMPLE 1

5-t-butyl-3-benzyl-6,8-dioxa-3-azabicyclo [3.2.1] octane maleate (I)

Code number: 29

A solution of 52 g of 2,2-dimethyl-4-[N-benzyl-N-(1-(3,3-dimethyl-2-butanoyl)) aminomethyl]-1,3-dioxolane [(II), R₁=benzyl, R′=+, m=1] and 34.3 g of hydrated paratoluene sulfonic acid in 500 ml of benzene and 3 ml of water is brought to reflux for 6 hours. Then, the solvent is evaporated, the residue is taken up in an aqueous solution of sodium carbonate, the obtained solution is extracted with ethyl acetate, the extract is washed with water, dried on sodium sulfate, filtered, the filtrate is evaporated and the residue chromatographed on a silica column (eluent: methylene chloride 99%-acetone 1%). Then, the product obtained is dissolved in acetone, an acetone solution of maleic acid is added, the product obtained is filtered and recrystallized in alcohol. Thus 34.9 g of the expected product are obtained.

By the same process, but from the corresponding reagents, the derivatives of formula (I) are obtained which appear in table I below under the code numbers 1 to 28, 30, 31, 34 to 46, 49 to 53, 55 to 58, 60 and 62.

EXAMPLE 2

5-phenyl-3-benzyl-6,8-dioxa-3-azabicyclo [3.2.1] octane (I)

Code number: 34

1st step: N-benzyl, N-phenacyl amino-3 propanedio-1,2 [(IIa or (IIb), R₁=benzyl, R'=

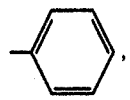

m=1]

A solution of 85 g of 2,2-dimethyl-4-(N-benzyl-N-phenacyl aminomethyl) 1,3-dioxolane [(II), R₁=benzyl, R+=

m=1] in 650 ml of 2N hydrochloric acid is stirred at 50° C. for 2 hours. Then, it is basified with an aqueous solution of sodium carbonate, extracted with ethyl acetate, the extract is washed with water, dried on sodium sulfate, filtered and the filtrate is evaporated. 71.6 g (yield: 82%) of the expected product is obtained in the form of an oil which is used in the next step.

By the same process, but from the corresponding reagents, all the other (IIa) or (IIb) formula compounds of the invention are obtained.

2nd step: 5-phenyl-3-benzyl-6,8-dioxa-3-azabicyclo [3.2.1] octane (I)

Code number: 34

A solution of 13 g of the formula (IIa) or (IIb) compound obtained in the previous step and 8.1 of paratoluenesulfonic acid in 250 ml of toluene is brought to reflux for 10 minutes. Then, it is basified with an aqueous solution of sodium carbonate, extracted with ethyl acetate, the extract is washed with water, dried on sodium sulfate, filtered, the filtrate is evaporated and the residue crystallized in hexane. Thus 7 g of the expected compound are isolated.

By the same process, but from the corresponding reagents, the formula (I) derivatives are obtained which appear in table I below under the code numbers 1 to 31, 35 to 46, 49 to 53, 55 to 58, 60 and 62.

EXAMPLE 3

2,2-dimethyl-4-(N-benzyl-N-phenacyl aminomethyl)-1,3-dioxolane [(II), R₁=benzyl, R'=

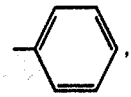

m=1]

A suspension of 63 g of phenacyl bromide (IV) and 66 g of 4-benzylaminomethyl-2,2-dimethyl-1,3-dioxolane [(III), R₁=benzyl] and 123 g of potassium carbonate in 1500 ml of benzene is brought to reflux for 6 hours. Then, the solvent is evaporated, the residue is taken up in water, extracted with ethyl acetate, the extract is washed with water, dried on sodium sulfate, filtered and the filtrate evaporated. 85 g (yield: 86%) of the expected product are obtained which is in the form of an oil.

By the same process, but from the corresponding reagents, all the other formula (II) compounds of the invention are obtained.

EXAMPLE 4

3-benzyl-7-parafluorophenyl-8,10-dioxa-3-azabicyclo [5.2.1] decane (I)

Code number: 33

1st step: 2-parafluorophenyl-2-[(3-chloropropyl)-1]4-chloromethyl-1,3-dioxolane (VI)

A solution of 55 g of 3 chloro-1,2 propanediol, 30 g of para-fluoro γ-chlorobutyrophenone [(VIII), R''=

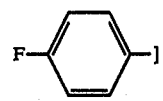

and 60 g of N-formyl morpholine dimethylsulfate

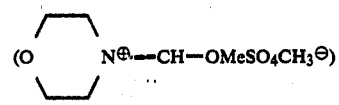

in 400 ml of methylene chloride is left under agitation for 4 days at 20° C. Then, it is washed with a 10% aqueous solution of sodium carbonate, then with water, dried on sodium sulfate, filtered, the filtrate is evaporated and the residue distilled. Thus 41 g (yield: 93%) of the expected compound are obtained.

Eb₀.₀₂=110° C.

By the same process, but from the corresponding reagents, the other formula (VI) compounds of the invention are obtained.

2nd step: 2-(1-(3-benzylaminopropyl))-2-parafluorophenyl-4-chloromethyl-1,3-dioxolane [(V), R'₁=benzyl, R''=

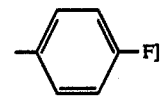

A mixture of 42.8 g of benzylamine and 57 g of the formula (VI) compound obtained in the previous step is brought to 75° C. for 20 hours. Then, it is diluted with ether, filtered, the filtrate is evaporated, the excess benzylamine is distilled and the residue is chromatographed on a silica column (eluent: 95% methylene chloride-5% methanol). Thus, 32.5 g (yield=47%) of the expected product is obtained in the form of an oil.

By the same process, but from the corresponding reagents, the other formula (V) compounds of the invention are obtained.

3rd step: 3-benzyl-7-parafluorophenyl-8,10-dioxa-3-azabicyclo [5.2.1] decane (I)

Code number: 33

20 g of the formula (V) compound described in the previous step is heated at 160° C. in 100 ml of tri-n-butylamine for 23 hours, then it is taken up in methylene chloride, the solution obtained is washed with water, dried on sodium sulfate, filtered, the filtrate is evaporated, the excess amine is distilled and the residue chromatographed on a silica column (eluent: 90% heptane—10% ethyl acetate). Thus, 5.4 g of the expected product are obtained.

EXAMPLE 5

5-parafluorophenyl-6,8-dioxa-3-azabicyclo [3.2.1] octane meleate (I)

Code number: 7

A suspension of 10.2 g of the formula (I) derivative of code No. 7 [$R_1$=benzyl, R=

n=1] prepared in example 7 and 1 g of palladium on charcoal (10% of palladium) in 250 ml of ethanol is agitated in an autoclave, for 3 hours at room temperature under a hydrogen pressure of 150 millibars. Then, it is filtered, the filtrate is evaporated, the residue dissolved (compound of code No. 7 in base form, melting point=89° C.) in acetone and an acetone solution of maleic acid is added. The mixture obtained is filtered and the precipitate formed is recrystallized in ethanol. Thus, 6.7 g of the expected product are obtained.

By the same process, but from the corresponding reagents, the formula (I) derivatives are obtained which appear in Table I below under the code numbers 1 to 6, 8 to 23, 32, 36, 38 to 40, 42, 44, 46, 48,51,53,56,58, 61 and 62.

EXAMPLE 6

3-methyl-5-parafluorophenyl-6,8-dioxa-3-azabicyclo [3.2.1] octane maleate (I)

Code number: 24

To a solution of 3 g of the formula (I) derivative of code No. 7 (prepared in example 5) and 1 g of benzyl tri-n-butylammonium bromide in 60 ml of toluene are added 3.5 g of methyl sulfate, then 60 ml of 50% NaOH and the mixture is heated to 60° C. for an hour. Then, it is decanted, the aqueous phase is extracted with toluene, the assembled organic phases are washed with water, dried on sodium sulfate, filtered, the filtrate is evaporated, the residue is dissolved in 20 ml of ethanol and an ethanol solution of maleic acid is added. The precipitate obtained is filtered and recrystallized in ethanol. Thus, 2.7 g of the expected compound are obtained.

By the same process, but from the corresponding reagents, the formula (I) derivatives are obtained which appear in Table I below under code numbers 25 to 28.

EXAMPLE 7

5-parafluorophenyl-3-benzyl-6,8-dioxa-3-azabicyclo [3.2.1] octane maleate (I)

Code number: 7a

To a solution of 21.8 g of 3-(N-benzyl-N-parafluorobenzoyl-methyl) amino-1,2-propanediol [(IIa) or (IIb)] in 300 ml of toluene are added 14.6 g of paratoluene sulfonic acid and the solution is heated to reflux for 10 minutes. Then, the toluene is evaporated, the residue is taken up in a chloroform-sodium carbonate aqueous solution mixture, the obtained solution is dried on sodium sulfate, filtered, the filtrate is evaporated, the residue (18.8 g; melting point: 85° C.) is dissolved in 200 ml of acetone and a solution of 7.5 g of maleic acid in 150 ml of acetone is added. The precipitate obtained is filtered and recrystallized in ethanol. Thus, the expected product is obtained with a yield of 90%.

EXAMPLE 8

3-benzyl-5-(3-pyridyl)-3-aza-6,8-dioxabicyclo [3.2.1] octane (I)

Code number: 47

1st step: 2-hydroxy-2-(3-pyridyl)-4-benzyl-6-(paratoluene sulfonyloxymethyl)morpholine [(IIc), $R'''_1=CH_2\phi$, m=1]

To a solution of 23.7 g of 2-hydroxy-2-hydroxymethyl-3-benzyl-2-(3-pyridinyl) morpholine (IIb) in 200 ml of pyridine are added 30.5 g of tosyl chloride. Then, after 3½ hours at room temperature, it is diluted with water, the mixture obtained is extracted with ethyl acetate, the extract is washed with water, dried on magnesium sulfate, filtered and the filtrate is evaporated; thus, 31.2 g (yield: 87%) of the expected product are obtained.

2nd step: 3-benzyl-5-(3-pyridyl)-3-aza-6,8-dioxabicyclo [3.2.1] octane (I)

A solution of 31.2 g of the compound (IIc), obtained in the previous step, in 300 ml of toluene and 45 ml of triethylamine is heated to reflux for 3 hours, then it is washed with water, dried on magnesium sulfate, filtered, the filtrate is evaporated and the residue is chromatographed on a silica column (medium pressure liquid chromatography), elution being effected with an ethyl acetate (80%)—heptane (20%) mixture. Thus, 8.1 g (yield=42%) of the expected product are obtained which is in the form of an oil.

EXAMPLE 9

4-(6,8-dioxa-3-azabicyclo [3.2.1] 5-octanoyl] benzoic acid chlorhydrate (I)

Code number: 54

To a solution of 2.6 g of sodium in 200 ml of ethanol are added 7.2 g of the derivative of formula (I), code number 62, and the solution is heated to reflux for 3 hours. Then the solvent is evaporated, the residue is taken up in water, the solution obtained is acidified with acetic acid and evaporated. The residue is dissolved in water and 10 N hydrochloric acid is added, the solvents are concentrated to 30 ml, then the precipitate obtained is filtered and rinsed on the filter with acetone, then with ether. Thus, 2.5 g (yield=34%) of the expected product are obtained.

EXAMPLE 10

5-(metabenzoyl) phenyl-3-aza-6,8-dioxabicyclo [3.2.1] octane chlorhydrate (I)

Code number: 59

A mixture of 10 g of 5-meta-hydroxy-phenyl) tolyl-3-aza-6,8-dioxabicyclo [3.2.1] octane [(I), code No. 61, obtained as in example 5, but from the derivative (I), of code No. 60] and 100 g of manganese dioxide in 400 ml of chloroform is heated to reflux for 90 minutes. Then it is filtered, the solvent is evaporated, the residue is dissolved in acetone, an acetone solution of maleic acid is added, the precipitate obtained is filtered, dissolved in water, the solution obtained is basified with sodium carbonate, extracted with methylene chloride, washed with water, dried on sodium sulfate and the filtrate evaporated. The residue is dissolved in acetone and 4 N hydrochloric ethanol is added. The precipitate obtained is filtered and washed on the filter with acetone, then with ether. Thus, 3.4 g (yield=82%) of the expected product are obtained.

TABLE I (I)

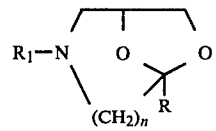

| Code number | R— | $R_1$ | n | Form | Empirical formula | Molecular weight | Melting point (°C.) | ELEMENTARY ANALYSIS | % | C | H | N |
|---|---|---|---|---|---|---|---|---|---|---|---|---|
| 1 | tert-butyl (−C(CH₃)₃) | H | 1 | hydrochloride | $C_9H_{18}ClNO_2$ | 207.70 | 220 | | Cal. Obt. | 52.04 52.22 | 8.74 8.83 | 6.74 6.89 |
| 2 | cyclohexyl | " | " | hydrochloride | $C_{11}H_{20}ClNO_2$ | 233.73 | 206 | | Cal. Obt. | 56.52 56.77 | 8.63 8.97 | 5.99 5.93 |
| 3 | phenyl | " | " | Maleate | $C_{15}H_{17}NO_6$ | 307.29 | 193 | | Cal. Obt. | 58.62 58.59 | 5.58 5.45 | 4.56 4.27 |
| 4 | 2-thienyl | " | " | Maleate | $C_{13}H_{15}NO_6S$ | 313.32 | 202 | | Cal. Obt. | 49.83 49.54 | 4.83 4.80 | 4.47 4.25 |
| 5 | 2-fluorophenyl | " | " | hydrochloride | $C_{11}H_{13}ClFNO_2$ | 245.68 | 160 | | Cal. Obt. | 53.77 54.03 | 5.33 5.10 | 5.70 5.55 |
| 6 | 3-fluorophenyl | " | " | hydrochloride | $C_{11}H_{13}ClFNO_2$ | 245.68 | 180 | | Cal. Obt. | 53.77 53.82 | 5.33 5.32 | 5.70 5.74 |
| 7 | 4-fluorophenyl | " | " | Maleate | $C_{15}H_{16}FNO_6$ | 325.29 | 203 | | Cal. Obt. | 55.38 55.64 | 4.96 4.74 | 4.31 4.22 |
| 8 | 2-chlorophenyl | " | " | hydrochloride | $C_{11}H_{13}Cl_2NO_2$ | 262.14 | 180 | | Cal. Obt. | 50.40 50.55 | 5.00 4.98 | 5.34 5.29 |
| 9 | 3-chlorophenyl | " | " | Maleate | $C_{15}H_{16}ClNO_6$ | 341.74 | 170 | | Cal. Obt. | 52.72 53.00 | 4.72 4.63 | 4.10 4.27 |
| 10 | 4-chlorophenyl | " | " | hydrochloride | $C_{11}H_{13}Cl_2NO_2$ | 262.14 | 190 | | Cal. Obt. | 50.40 50.25 | 5.00 5.05 | 5.34 5.44 |
| 11 | 2-methylphenyl | " | " | hydrochloride | $C_{12}H_{16}ClNO_2$ | 241.71 | 180 | | Cal. Obt. | 59.62 59.68 | 6.67 6.75 | 5.80 5.87 |
| 12 | 3-methylphenyl | " | " | Maleate | $C_{16}H_{19}NO_6$ | 321.32 | 182 | | Cal. Obt. | 59.80 59.81 | 5.96 6.12 | 4.36 4.39 |
| 13 | 4-methylphenyl | " | " | hydrochloride | $C_{12}H_{16}ClNO_2$ | 241.71 | 160 | | Cal. Obt. | 59.62 59.44 | 6.67 6.79 | 5.80 5.66 |
| 14 | 2-methoxyphenyl | " | " | Maleate | $C_{16}H_{19}NO_7$ | 337.32 | 182 | | Cal. Obt. | 56.97 57.11 | 5.68 5.62 | 4.15 4.11 |

TABLE I-continued (I)

$$R_1-N\underset{(CH_2)_n}{\diagup}O\underset{R}{\diagup}O$$

| | R₁ | | n | Salt | Formula | MW | mp | | C | H | N |
|---|---|---|---|---|---|---|---|---|---|---|---|
| 15 | 3-OCH₃-C₆H₄ | " | " | Maleate | C₁₆H₁₉NO₇ | 337.32 | 175 | Cal.<br>Obt. | 56.97<br>56.84 | 5.68<br>5.60 | 4.15<br>4.38 |
| 16 | 4-OCH₃-C₆H₄ | " | " | Maleate | C₁₆H₁₉NO₇ | 337.32 | 172 | Cal.<br>Obt. | 56.97<br>57.27 | 5.68<br>5.90 | 4.15<br>4.20 |
| 17 | 3-CF₃-C₆H₄ | " | " | Maleate | C₁₆H₁₆F₃NO₆ | 375.30 | 176 | Cal.<br>Obt. | 51.20<br>51.31 | 4.30<br>4.08 | 3.73<br>3.76 |
| 18 | 4-CF₃-C₆H₄ | " | " | Base | C₁₂H₁₂F₃NO₂ | 259.22 | 72 | Cal.<br>Obt. | 55.60<br>55.39 | 4.67<br>4.35 | 5.40<br>5.21 |
| 19 | 4-CN-C₆H₄ | " | " | Maleate | C₁₆H₁₆N₂O₆ | 332.30 | 215 | Cal.<br>Obt. | 57.83<br>57.93 | 4.85<br>4.55 | 8.43<br>8.71 |
| 20 | 3-OH-C₆H₄ | " | " | hydro-<br>chloride | C₁₁H₁₄ClNO₃ | 243.69 | 190 | Cal.<br>Obt. | 54.21<br>54.37 | 5.79<br>5.75 | 5.75<br>5.47 |
| 21 | 4-NO₂-C₆H₄ | " | " | hydro-<br>chloride | C₁₁H₁₃ClN₂O₄ | 272.69 | 240 | Cal.<br>Obt. | 48.45<br>48.53 | 4.81<br>4.85 | 10.27<br>10.15 |
| 22 | 3,5-Cl₂-C₆H₃ | " | " | hydro-<br>chloride | C₁₁H₁₂Cl₃NO₂ | 296.58 | 175 | Cal.<br>Obt. | 44.54<br>44.83 | 4.08<br>4.00 | 4.72<br>4.83 |
| 23 | 3,4-Cl₂-C₆H₃ | " | " | hydro-<br>chloride | C₁₁H₁₂Cl₃NO₂ | 296.58 | 220 | Cal.<br>Obt. | 44.54<br>44.51 | 4.08<br>4.01 | 4.72<br>4.63 |
| 24 | 4-F-C₆H₄ | CH₃ | " | Maleate | C₁₆H₁₈FNO₆ | 339.31 | 198 | Cal.<br>Obt. | 56.63<br>56.62 | 5.35<br>5.39 | 4.13<br>3.83 |
| 25 | " | Et | " | Maleate | C₁₇H₂₀FNO₆ | 353.34 | 180 | Cal.<br>Obt. | 57.78<br>57.78 | 5.71<br>5.69 | 3.96<br>3.90 |
| 26 | " | iPr | " | Maleate | C₁₈H₂₂FNO₆ | 367.36 | 189 | Cal.<br>Obt. | 58.85<br>58.84 | 6.04<br>6.13 | 3.81<br>3.68 |
| 27 | " | tBu | " | Maleate | C₁₉H₂₄FNO₆ | 381.39 | 182 | Cal.<br>Obt. | 59.83<br>59.75 | 6.34<br>6.48 | 3.67<br>3.70 |
| 28 | " | C₆H₁₁ | " | Maleate | C₂₁H₂₆FNO₆ | 407.43 | 170 | Cal.<br>Obt. | 61.90<br>61.83 | 6.43<br>6.61 | 3.44<br>3.41 |
| 29 | tBu | CH₂—φ | " | Maleate | C₂₀H₂₇NO₆ | 377.33 | 206 | Cal.<br>Obt. | 63.66<br>63.63 | 7.21<br>7.32 | 3.71<br>3.70 |
| 30 | " | C₆H₁₁ | " | Maleate | C₂₂H₂₉NO₆ | 402.46 | 189 | Cal.<br>Obt. | 65.49<br>65.36 | 7.25<br>7.48 | 3.47<br>3.39 |
| 31 | 4-F-C₆H₄ | " | 2 | hydro-<br>chloride | C₁₉H₂₁ClFNO₂ | 349.82 | 200 | Cal.<br>Obt. | 65.23<br>65.08 | 6.05<br>6.05 | 4.00<br>3.97 |

TABLE I-continued (I)

$$R_1-N\begin{matrix}\diagup\\\diagdown(CH_2)_n\end{matrix}\begin{matrix}O\\\diagdown C\diagup\\R\end{matrix}O$$

| Code No. | R— | R₁ | n | Form | Empirical formula | Molecular weight | Melting point (°C.) | | ELEMENTARY ANALYSIS or NMR SPECTRUM | | |
|---|---|---|---|---|---|---|---|---|---|---|---|
| | | | | | | | | % | C | H | N |
| 32 | " | H | 3 | hydro-chloride | C₁₃H₁₇ClFNO₂ | 273.73 | 180 | Cal. | 57.04 | 6.26 | 5.12 |
| | | | | | | | | Obt. | 56.86 | 5.98 | 4.86 |
| 33 | " | CH₂—φ | " | Base | C₂₀H₂₂FNO₂ | 327.38 | 76 | Cal. | 77.37 | 6.77 | 4.28 |
| | | | | | | | | Obt. | 73.31 | 6.99 | 4.15 |
| 34 |  | " | 1 | Base | C₁₈H₁₉NO₂ | 281.34 | <50 | Cal. | 76.84 | 6.81 | 4.98 |
| | | | | | | | | Obt. | 76.66 | 6.99 | 5.02 |

| Code No. | R— | R₁ | n | Form | Empirical formula | Molecular weight | Melting point (°C.) | ELEMENTARY ANALYSIS or NMR SPECTRUM |
|---|---|---|---|---|---|---|---|---|
| | | | | | | | | % C H N |
| 35 |  | Benzyl | 1 | Base | C₂₂H₂₉NO₂ | 339.46 | 147 | NMR (CDCl₃); δ ppm = 7.30, s (5 aromatic H); 4.4, m (H in 1); 4.15, d (H β in 7); 3.75, t (H α in 7); 3.5, d (CH₂—φ); 2.4 to 3, m (4 H in 2 and 4); 1.5 to 2, m (adamantylic H) |
| 36 | " | H | " | HCl | C₁₅H₂₄ClNO₂ | 285.81 | >260 | Cal. 63.03 8.46 4.90 |
| | | | | | | | | Obt. 62.62 8.48 4.87 |
| 37 | —CH₂—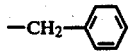 | Benzyl | " | Base | C₁₉H₂₁NO₂ | 295.37 | 99 | NMR (CDCl₃); δ ppm = 7.2, s (10 aromatic H); 4.35, m (H in 1); 4.1, d (H β in 7); 3.8, t (H α in 7); 3.4, d (⟩N—CH₂—φ); 2.9, s (CH₂ φ); 2 to 2.8, m (H in 2 and 4) |
| 38 | " | H | " | HCl + 2.9% H₂O | C₁₂H₁₆ClNO₂ + 2.9% H₂O | 248.78 | 220 | Cal. 57.93 6.80 5.64 |
| | | | | | | | | Obt. 57.96 6.78 5.69 |
| 39 | 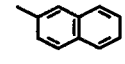 | " | " | HCl | C₁₅H₁₆ClNO₂ | 277.74 | 210 | Cal. 64.86 5.81 5.04 |
| | | | | | | | | Obt. 64.86 6.12 5.07 |
| 40 | 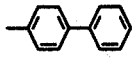 | " | " | Base | C₁₇H₁₇NO₂ | 267.31 | 129 | Cal. 76.38 6.41 5.24 |
| | | | | | | | | Obt. 76.00 6.46 5.10 |
| 41 | 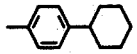 | Benzyl | " | Base | C₂₄H₂₉NO₂ | 363.48 | Oil | NMR (CDCl₃) δ ppm = 7.4, m (9 aromatic H); 4.6, m (H in 1); 4.4, d (H β in 7); 3.95, t (H α in 7); 3.6, d (N—CH₂φ); 2.4 to 3.2, m (H in 2 and 4 and 1 cyclohexanic H); 1.2 to 2, m (10 cyclohexanic H) |
| 42 | 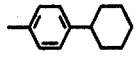 | H | " | HCl + 2.5% H₂O | C₁₇H₂₄ClNO₂ + 2.5% H₂O | 317.87 | 219 | Cal. 64.23 7.57 4.41 |
| | | | | | | | | Obt. 64.38 7.97 4.33 |
| | | | | Base | C₁₇H₂₃NO₂ | 273.36 | 116 | |
| 43 | 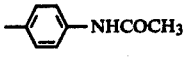—NHCOCH₃ | Benzyl | " | Base | C₂₀H₂₂N₂O₃ | 338.39 | 90 | NMR (CDCl₃) δ ppm = 7.6, m (NH CO); 7.45, s and 7.3, s (9 aromatic H); 4.6, m (H in 1); 4.35, d (H β in 7); 3.9, t (H α in 7); 3.6, d (N—CH₂φ); 2.3 to 3.1, m (H in 2 and 4); 2.1, s (CH₃CO) |
| 44 | " | H | " | Base | C₁₃H₁₆N₂O₃ | 248.27 | 168 | Cal. 62.89 6.50 11.28 |
| | | | | | | | | obt. 62.58 6.82 11.47 |
| 45 | 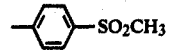—SO₂CH₃ | Benzyl | " | Base | C₁₉H₂₁NO₄S | 359.43 | 158 | NMR (CDCl₃) δ ppm = 7.8, m (4 aromatic H); 7.3, s (5 aromatic H); 4.65, m (H in 1); 4.35, d (H β in 7); 3.9, t (H α in 7); 3.6, s (N—CH₂φ); 3.0, s (CH₃SO₂); 2.3 to 3.1, m (H in 2 and 4) |
| 46 | " | H | " | Base | C₁₂H₁₅NO₄S | 269.31 | 181 | Cal. 53.51 5.61 5.20 |
| | | | | | | | | Obt. 53.53 5.90 5.10 |

TABLE I-continued $$R_1-N\underset{(CH_2)_n}{\overset{O}{\diagdown}}\overset{O}{\underset{R}{\diagup}}\quad(I)$$

| # | R₁ sub | R₁ | | Form | Formula | MW | mp/state | Analysis / NMR |
|---|---|---|---|---|---|---|---|---|
| 47 | 3-pyridyl | Benzyl | " | Base | C₁₇H₁₈N₂O₂ | 282.33 | Oil | NMR (CDCl₃) δ ppm = 8.85, m, 8.55, m and 7.8, m (3 pyridinic H); 7.25, m + s (1 pyridinic H and 5 aromatic H); 4.6, m (H in 1); 4.35, d (H β in 7); 3.9, t (H α in 7); 3.6, d (N—CH₂φ); 2.3 to 3.1, m (H in 2 and 4) |
| 48 | " | H | " | diHCl | C₁₀H₁₄ClN₂O₂ | 265.14 | 150 | Cal. 45.30 5.32 10.57 / Obt. 45.46 5.67 10.53 |
| 49 | 3-NO₂-phenyl | " | " | HCl | C₁₁H₁₃ClN₂O₄ | 272.69 | 200 | Cal. 48.45 4.81 10.27 / Obt. 48.36 5.02 10.32 |
| 50 | 3-phenoxyphenyl | Benzyl | " | Base | C₂₄H₂₃NO₃ | 373.43 | Oil | NMR (CDCl₃) δ ppm = 6.8 to 7.4, m (14 aromatic H); 4.5, m (H in 1); 4.3, d (H β in 7); 3.9, t (H α in 7); 3.55, d (N—CH₂φ); 2.3 to 3.1, m (H in 2 and 4) |
| 51 | 3-phenoxyphenyl | H | " | HCl | C₁₇H₁₈ClNO₃ | 319.78 | 180 | Cal. 63.84 5.67 4.38 / Obt. 63.54 5.67 4.28 |
| 52 | 4-CONH₂-phenyl | Benzyl | " | Base | C₁₉H₂₀N₂O₃ | 324.37 | Oil | NMR (CDCl₃) δ ppm = 7.3, s and 7.3 to 8.0, m (CONH₂ and 9 aromatic H); 4.6, m (H in 1); 4.2, d (H β in 7); 3.9, t (H α in 7); 3.55, s (N—CH₂φ); 2.3 to 3, m (H in 2 and 4). |
| 53 | " | H | " | Base | C₁₂H₁₄N₂O₃ | 234.25 | 198 | Cal. 61.52 6.02 11.96 / Obt. 61.53 6.15 11.94 |
| 54 | 4-COOH-phenyl | H | " | HCl + 2.3% H₂O | C₁₂H₁₄ClNO₄ + 2.3% H₂O | 271.70 | 180 | Cal. 51.82 5.33 5.04 / Obt. 51.93 5.36 4.99 |
| 55 | 6-methoxy-2-naphthyl | Benzyl | " | Base | C₂₃H₂₃NO₃ | 361.42 | 130 | NMR (CDCl₃) δ ppm = 7.3, s and 7 to 8, m (11 aromatic H); 4.6, m (H in 1); 4.35, d (H β in 7); 3.9, t (H α in 7); 3.85, s (CH₃O—); 3.6, d (N—CH₂φ); 2.4 to 3.2, m (H in 2 and 4) |
| 56 | " | H | " | Base | C₁₆H₁₇NO₂ | 271.30 | 117 | Cal. 70.83 6.32 5.16 / Obt. 70.91 6.60 5.25 |
| 57 | 1-naphthyl | Benzyl | " | Base | C₂₂H₂₁NO₂ | 331.40 | Oil | NMR (CDCl₃) δ ppm = 8.1, m, 7.3, s and 7.2 to 8, m (12 aromatic H); 4.65, m (H in 1); 4.4, d (H β in 7); 4.95, t (H α in 7); 3.55, d (N—CH₂φ); 2.4 to 3.1, m (H in 2 and 4) |
| 58 | " | H | " | HCl | C₁₅H₁₆ClNO₂ | 277.74 | 210 | Cal. 64.86 5.81 5.04 / Obt. 64.58 5.94 5.07 |
| 59 | 3-phenoxycarbonyl-phenyl | " | " | HCl | C₁₈H₁₈ClNO₃ | 331.79 | 180 | Cal. 65.16 5.47 4.22 / Obt. 64.98 5.75 4.20 |
| 60 | " | " | " | Base | C₂₅H₂₃NO₃ | 385.44 | Oil | NMR (CDCl₃) δ ppm = 7.2 to 8, m (14 aromatic H); 4.6, m (H in 1); 4.3, d (H β in 7); 3.9, t (H α in 7); 3.55, d (N—CH₂—φ); 2.4 to 3.1, m (H in 2 and 4) |
| 61 | 3-(α-hydroxybenzyl)phenyl | H | " | Base | C₁₈H₁₉NO₃ | 297.34 | 127 | Cal. 72.70 6.44 4.71 / Obt. 72.47 6.62 4.81 |

TABLE I-continued

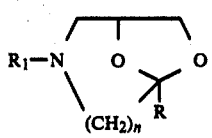

| | | | | | | | | | | |
|---|---|---|---|---|---|---|---|---|---|---|
| 62 | EtOCO-⟨⟩- | " | " | HCl | C$_{14}$H$_{18}$ClNO$_4$ | 229.75 | 179 | Cal. | 56.09 | 6.05 | 4.67 |
| | | | | | | | | Obt. | 56.09 | 6.14 | 4.66 |

The derivatives of formula (I) and the acid addition salts thereof have been tested on laboratory animals and showed pharmacological properties, particularly an analgesic activity. This latter activity was displayed in mice with the analgesia test using phenylbenzoquinone according to the method described by E. SIEGMUND; R. CADMUS and G.LU in Proc. Soc. Exp. Biol. Med. 95, 729(1957).

The compounds of the invention were administered intraperitoneally.

Acute toxicity was evaluated intraperitoneally in mice according to the method described by MILLER and TAINTER in Proc. Soc. Exp. Biol. Med. 57, 261 (1944).

To illustrate the invention, the results obtained in these tests with some of the compounds of the invention are shown in Table II below.

TABLE II

| Code number of compounds tested | Acute toxicity (mice) LD 50 (mg/kg/i.p.) | Analgesia test (mice) ED 50 (mg/kg/i.p.) |
|---|---|---|
| 1 | 400 | 18 |
| 4 | >400 | 24 |
| 7 | 300 | 10 |
| 9 | 240 | 10 |
| 14 | 300 | 8 |
| 19 | 280 | 19 |
| 21 | 290 | 10 |
| 23 | 300 | 10 |
| 25 | 280 | 14 |
| 30 | >400 | 26 |
| 32 | 140 | 9 |
| 36 | 185 | 30 |
| 39 | 310 | 8 |
| 40 | 310 | 24 |
| 42 | >400 | 15 |
| 44 | 380 | 7 |
| 48 | >400 | 58 |
| 54 | >400 | 38 |
| 56 | 240 | 21 |
| 58 | 160 | 28 |
| 59 | 155 | 13.5 |

As table II shows, the difference between toxic doses and active doses allows the derivatives of formula (I) and their pharmaceutically acceptable salts to be used in therapeutics, particularly for treating pains of different origins.

The present invention also provides then, as medicaments and particularly as analgesic medicaments, the derivatives of formula (I) and their pharmaceutically acceptable acid addition salts.

The invention extends to pharmaceutical compositions comprising, as active ingredient, at least one of the medicaments such as they have just been defined, in association with a pharmaceutically acceptable vehicle.

These compositions may be administered orally in the form of pills, tablets or capsules, in a dose up to 0.5 g of active ingredient/day, intramuscularly in the form of injectable ampoules containing up to 2.5 g of active ingredient (1 to 2 per day) or rectally in the form of suppositories containing up to 1 g of active ingredient (1 to 3 per day).

We claim:

1. A compound having the formula:

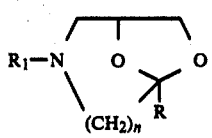

wherein R$_1$ is hydrogen, alkyl having 1 to 4 carbon atoms, cyclohexyl or benzyl; R is selected from the group consisting of (1) alkyl having at least 4 carbon atoms, (2) cyclohexyl, (3) unsubstituted phenyl or phenyl substituted with one or more halogen atoms, or by a methyl, methoxy, hydroxy, cyano, nitro, trifluoromethyl, carboxyl, ethoxycarbonyl, acetamido, methylsulfonyl, phenoxy, benzoyl, phenyl, α-hydroxybenzyl, cyclohexyl or carbamoyl, (4) thienyl, (5) pyridyl, (6) naphthyl, (7) methoxy-substituted naphthyl; (8) adamantyl and (9) benzyl; and n is 1, 2 or 3, with the provisos that (a) when R is carboxyphenyl, benzoylphenyl, or (α-hydroxybenzyl)phenyl, n is not 3, and (b) when R is (60 -hydroxybenzyl) phenyl, R$^1$ is not benzyl, and pharmacologically aceeptable acid addition salts thereof.

2. A compound as claimed in claim 1, wherein R$_1$=H and n=1 or 3.

3. A compound as claimed in claim 2, wherein the pair (n, R) takes on one of the following meanings:

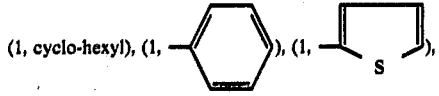

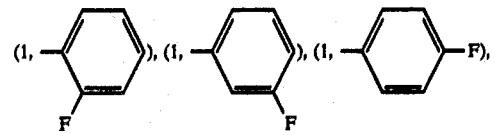

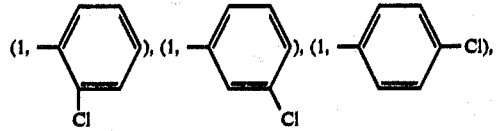

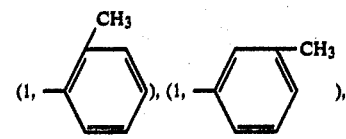

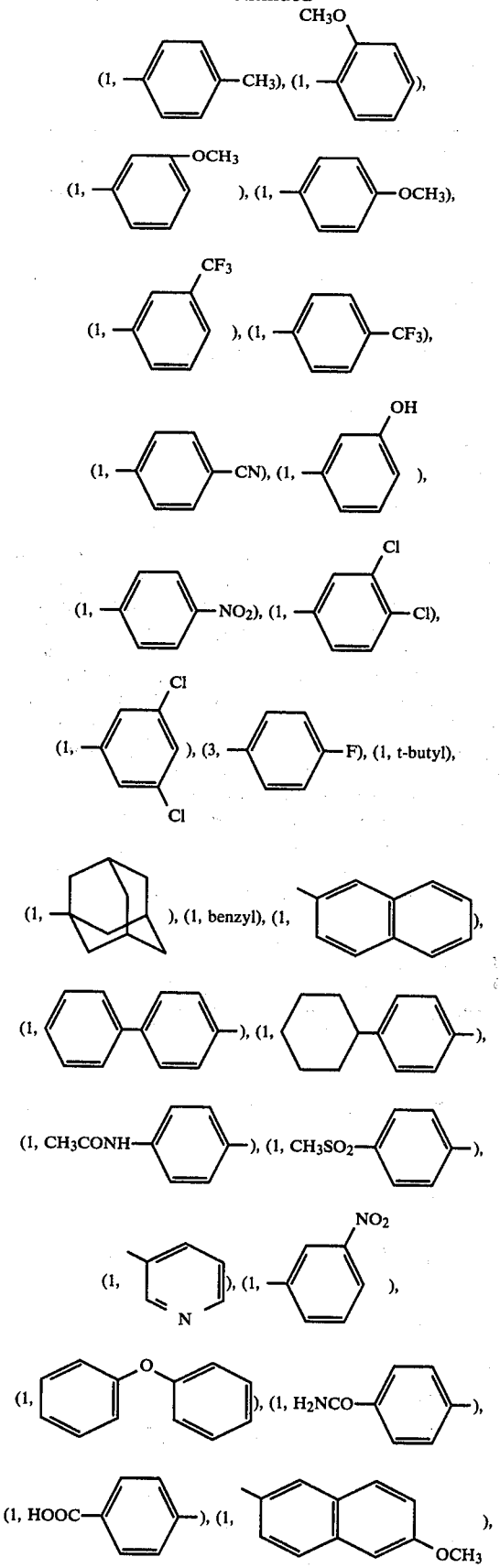
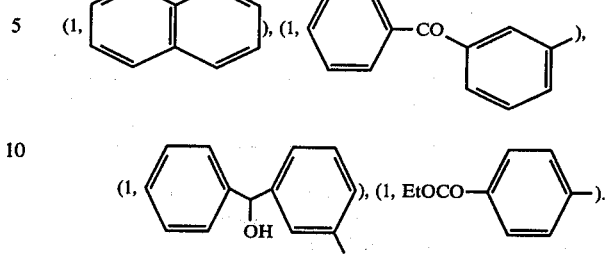

4. A compound as claimed in claim 1, wherein R represents the parafluorophenyl group and the pair (n, $R_1$) takes on any one of the following meanings: (1, $CH_3$), (1, Et), (1, isopropyl), (1, tert-butyl), (1, cyclohexyl), (2, benzyl), (3, benzyl).

5. A compound as claimed in claim 1, wherein $R_1$ is cyclohexyl or benzyl.

6. A compound as claimed in claim 1, wherein R is selected from (2), (3), (4), (5), (6), (7), (8) and (9).

7. A compound as claimed in claim 1, wherein said acid used to form said acid addition salt is hydrochloric acid or maleic acid.

8. A compound according to claim 1 in which R is (3) unsubstituted phenyl or phenyl substituted with one or more halogens, methyl, methoxy, hydroxy, cyano, nitro, trifluoromethyl, carboxyl, ethoxycarbonyl, acetamido, methylsulfonyl, phenoxy, benzoyl, phenyl, α-hydroxybenzyl, cyclohexyl or carbamoyl.

9. A compound according to claim 1 in which R is phenyl substituted with one or more halogens, methyl, methoxy, hydroxy, cyano, nitro or trifluoromethyl.

10. A compound according to claim 9 in which $R_1$ is hydrogen.

11. A compound according to claim 9 in which $R_1$ is benzyl.

12. A compound according to claim 1 in which R is unsubstituted naphthyl or naphthyl substituted with methoxy.

13. A compound according to claim 12 in which $R_1$ is hydrogen.

14. A compound according to claim 12 in which $R_1$ is benzyl.

15. A compound according to claim 1, havin the formula

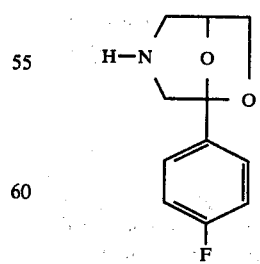

and pharmacologically acceptable acid addition salts thereof.

16. A compound according to claim 1, having the formula

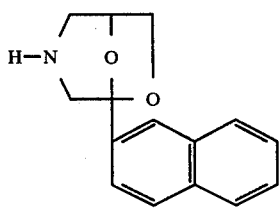

and pharmacologically acceptable acid addition salts thereof.

17. A compound according to claim 1, having the formula

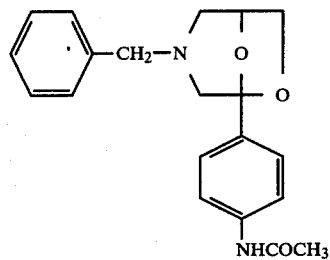

and pharmacologically acceptable acid addition salts thereof.

18. A compound according to claim 1, having the formula

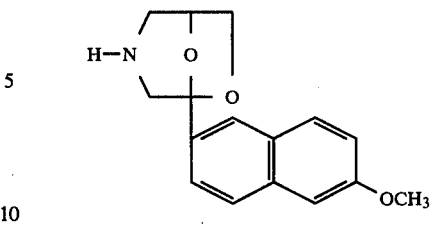

and pharmacologically acceptable acid addition salts thereof.

19. A compound according to claim 1, having the formula

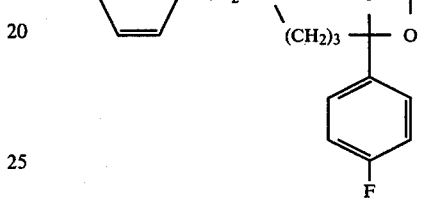

and pharmacologically acceptable acid addition salts thereof.

20. A pharmaceutical composition for treating pain comprising an effective amount of a compound as claimed in claim 1, in combination with a pharmaceutically acceptable carrier, diluent or vehicle.

21. A method for treating a subject suffering from pain comprising administering to said subject a therapeutically effective amount of the composition as claimed in claim 20.

* * * * *

UNITED STATES PATENT AND TRADEMARK OFFICE
CERTIFICATE OF CORRECTION

PATENT NO.  : 4 463 004
DATED       : July 31, 1984
INVENTOR(S) : Patrick G. Guerret et al It is certified that error appears in the above—identified patent and that said Letters Patent is hereby corrected as shown below:

Column 18, line 39; change "(60 -hydroxybenzyl) phenyl" to ---(α-hydroxybenzyl)phenyl---.

line 40; change "aceeptable" to ---acceptable---.

Column 20, line 50; change "havin" to ---having---.

Signed and Sealed this

Twenty-sixth Day of February 1985

[SEAL]

Attest:

DONALD J. QUIGG

*Attesting Officer*    *Acting Commissioner of Patents and Trademarks*